(12) United States Patent
Franke et al.

(10) Patent No.: US 9,694,341 B2
(45) Date of Patent: Jul. 4, 2017

(54) JET LOOP REACTOR WITH NANOFILTRATION AND GAS SEPARATOR

(71) Applicant: Evonik Degussa GmbH, Essen (DE)

(72) Inventors: Robert Franke, Marl (DE); Bart Hamers, RM Horst (NL)

(73) Assignee: Evonik Degussa GmbH, Essen (DE)

(*) Notice: Subject to any disclaimer, the term of this patent is extended or adjusted under 35 U.S.C. 154(b) by 0 days.

(21) Appl. No.: 15/030,036

(22) PCT Filed: Sep. 23, 2014

(86) PCT No.: PCT/EP2014/070194
§ 371 (c)(1),
(2) Date: Apr. 15, 2016

(87) PCT Pub. No.: WO2015/058919
PCT Pub. Date: Apr. 30, 2015

(65) Prior Publication Data
US 2016/0243519 A1      Aug. 25, 2016

(30) Foreign Application Priority Data
Oct. 25, 2013   (DE) ................... 10 2013 221 708

(51) Int. Cl.
| | |
|---|---|
| C07C 45/00 | (2006.01) |
| B01J 19/00 | (2006.01) |
| B01J 19/24 | (2006.01) |
| B01J 10/00 | (2006.01) |
| B01J 19/26 | (2006.01) |
| C07C 29/16 | (2006.01) |
| C07C 45/50 | (2006.01) |

(52) U.S. Cl.
CPC .......... B01J 19/2465 (2013.01); B01J 10/00 (2013.01); B01J 10/002 (2013.01); B01J 19/246 (2013.01); B01J 19/2475 (2013.01); B01J 19/26 (2013.01); C07C 29/16 (2013.01); C07C 45/50 (2013.01); *B01J 2219/00103* (2013.01); *B01J 2219/185* (2013.01)

(58) Field of Classification Search
CPC ..... C07C 45/505; B01J 19/24; B01J 19/2435; B01J 8/0065
USPC .......................... 568/429, 451; 422/189, 600
See application file for complete search history.

(56) References Cited

U.S. PATENT DOCUMENTS

| | | |
|---|---|---|
| 8,389,774 B2 | 3/2013 | Becker et al. |
| 9,149,780 B2 | 10/2015 | Hamers et al. |
| 2008/0251456 A1 | 10/2008 | Wiese et al. |
| 2009/0032465 A1 | 2/2009 | Baumgarten et al. |
| 2011/0114075 A1 | 5/2011 | Mills |
| 2012/0108852 A1 | 5/2012 | Greb et al. |
| 2015/0018576 A1 | 1/2015 | Baumgarten et al. |
| 2015/0299079 A1 | 10/2015 | Fridag et al. |
| 2015/0336078 A1 | 11/2015 | Hamers et al. |
| 2015/0336861 A1 | 11/2015 | Geilen et al. |
| 2016/0002136 A1 | 1/2016 | Lueken et al. |
| 2016/0082393 A1 | 3/2016 | Priske et al. |

FOREIGN PATENT DOCUMENTS

| | | |
|---|---|---|
| CN | 1966139 | 5/2007 |
| DE | 19632600 A1 | 2/1998 |
| DE | 10308111 A1 | 9/2004 |
| DE | 102005046250 A1 | 3/2007 |
| DE | 102006003618 A1 | 8/2007 |
| DE | 102009016652 A1 | 10/2010 |
| DE | 102012202779 A1 | 8/2013 |
| EP | 0781166 A1 | 8/2000 |
| WO | 2010023018 A1 | 3/2010 |

OTHER PUBLICATIONS

International Search Report, PCT/EP2014/070194, Dec. 5, 2014.
Written Opinion, PCT/EP2014/070194, Dec. 5, 2014.
Zehner, et al., "Bubble Columns", Ullmann's Encyclopedia of Industrial Chemistry, Electronic Release, 7th ed., Chapter 4, Wiley-VCH, Weinheim [2005].
Falbe, New Syntheses with Carbon Monoxide. Springer Verlag 1980, Berlin, Heidelberg, New York.
Cornils et al., "Applied Homogeneous Catalysis with Organometallic Compounds", vol. 1 & 2, VCH, Weinheim, New York, 1996.
Franke, et al., "Applied Hydroformylation", Chem. Rev., 2012, DOI:10.1021/cr3001803.
Melin / Rautenbach: Membranverfahren. Grundlagen der Modul— und Anlagenauslegung. [Membrane Processes. Fundamentals of Module and System Design] Springer, Berlin Heidelberg 2004.
Priske, et al.: Reaction integrated separation of homogeneous catalysts in the hydroformylation of higher olefins by means of organophilic nanofiltration. Journal of Membrane Science, vol. 360, Issues 1-2, Sep. 15, 2010, pp. 77-83; doi:10.1016/j.memsci.2010.05.002.
Janssen, et al. (2010), Continuous Rhodium-Catalyzed Hydroformylation of 1-Octene with Polyhedral Oligomeric Silsesquioxanes (POSS) Enlarged Triphenylphosphine. Angewandte Chemie International Edition, 49: 7738-7741. doi:10.1002/anie.201001926.

(Continued)

*Primary Examiner* — Sikarl Witherspoon
(74) *Attorney, Agent, or Firm* — Michael Best & Friedrich LLP (57) ABSTRACT

The invention relates to a device for the continuous homogeneous catalytic reaction of a liquid with a gas and optionally a further fluid, wherein the device comprises at least one jet loop reactor having an external liquid circuit driven by at least one pump, and wherein the device has at least one membrane separation unit, preferably retaining the homogeneous catalyst, which membrane separation unit is arranged in the external liquid circuit of the jet loop reactor. The object thereof is to reduce the costs of the device. This is achieved by providing an additional apparatus, namely a gas separator, which is arranged in the external liquid circuit of the jet loop reactor and is installed for separating off gas from the external liquid circuit and feeding it back into the jet loop reactor.

11 Claims, 3 Drawing Sheets

JET LOOP REACTOR WITH NANOFILTRATION AND GAS SEPARATOR

The invention relates to a device for the continuous homogeneous catalytic reaction of a liquid with a gas and optionally a further fluid, wherein the device comprises at least one jet loop reactor having an external liquid circuit driven by at least one pump, and wherein the device has at least one membrane separation unit, preferably retaining the homogeneous catalyst, which membrane separation unit is arranged in the external liquid circuit of the jet loop reactor.

A liquid is a substantially incompressible free-flowing medium. A gas is a compressible free-flowing medium. A fluid is a liquid or a gas. A two-phase mixture of a homogeneously distributed liquid phase and a gas phase dispersely distributed therein is likewise a fluid in the context of this invention. On account of the gas fraction, such fluids are to a small extent compressible.

In the context of the present invention, a fed liquid is taken to mean a substance or mixture of substances which is present in the liquid state of matter in the apparatus under reaction conditions and has at least one reactant. Gas is taken to mean a pure gas or a gas mixture which has at least one reactant and optionally one inert gas. One example of a gas which has two reactants is the synthesis gas consisting of hydrogen and carbon monoxide, which synthesis gas is used, for example, in hydroformylations.

A jet loop reactor in the context of the invention is a device for the continuous reaction of a liquid and at least one further fluid in which the liquid enters under pressure through a nozzle into a reaction space, flows therethrough along a main flow direction, is deflected at the reaction space end situated opposite the nozzle, flows back against the main flow direction and again is accelerated in the main flow direction, in such a manner that within the reactor space an internal liquid circuit (loop) is established. The second fluid is entrained by the liquid flow and reacts en route along the loop. The liquid therefore acts as driving jet medium. To input the kinetic energy into the liquid, an external liquid circuit is assigned to the reaction space, in which external liquid circuit some of the liquid is circulated in the circuit outside the reaction space. Within the external liquid circuit, a pump is provided which imparts the necessary kinetic energy to the liquid stream for establishing the loop flow within the reactor. The nozzle is accordingly fed from the external circuit.

A good introduction to the technique of jet loop reactors is offered in:
P. Zehner, M. Krause: "Bubble Columns", Ullmann's Encyclopedia of Industrial Chemistry, Electronic Release, 7th ed., Chapter 4, Wiley-VCH, Weinheim [2005].

In the hydroformylation (also termed oxo reaction), hydrocarbons having olefinic double bonds (alkenes) are reacted with synthesis gas (gas mixture of hydrogen and carbon monoxide) to form aldehydes and/or alcohols.

Fundamental introductions to hydroformylation are offered in: Falbe, Jürgen: New Syntheses with Carbon Monoxide. Springer Verlag 1980, Berlin, Heidelberg, New York und Pruett, Roy L.: Hydroformylation. Advances in Organometallic Chemistry Vol. 17, pages 1-60, 1979.

A good overview of the state of the hydroformylation of olefins may be found in
B. Cornils, W. A. Herrmann, "Applied Homogeneous Catalysis with Organometallic Compounds", Vol. 1 & 2, VCH, Weinheim, New York, 1996
and also in
R. Franke, D. Selent, A. Börner, "Applied Hydroformylation", Chem. Rev., 2012, DOI:10.1021/cr3001803.

Hydroformylation serves for production of higher aldehydes. Higher aldehydes, in particular those having 3 to 25 carbon atoms, are used, for example, as synthesis precursors, for producing carboxylic acids, and as odourants. Industrially they are frequently converted by catalytic hydrogenation to the corresponding alcohols, which in turn serve for the production of plasticizers and detergents. On account of the large scale industrial importance of the hydroformylation products, the oxo reaction is carried out on an industrial scale.

In the large scale industrial hydroformylation, currently organophosphorus metal complex catalysts based on cobalt or rhodium are used. The catalysts are homogeneously dissolved in the liquid hydroformylation mixture. In the context of separating out the target product (the aldehydes) from the hydroformylation mixture, the homogeneous catalyst must also be separated off under gentle conditions from the hydroformylation mixture, since the complex catalyst reacts comparatively sensitively to changes in state and could lose its activity.

Traditionally, the catalyst is separated off from the hydroformylation mixture by distillation. In order to reduce the risk of deactivation and to reduce the energy consumption of the process, recent efforts are being made to separate off the homogeneously dissolved catalyst from the hydroformylation mixture using membrane technology (nanofiltration). An excellent introduction into membrane technology is given by:
Melin/Rautenbach: Membranverfahren. Grundlagen der Modul-und Anlagenauslegung. [Membrane Processes. Fundamentals of Module and System Design] Springer, Berlin Heidelberg 2004.

The fundamentals of membrane-supported, organophilic nanofiltration for separating off homogenously dissolved catalyst complexes from hydroformylation mixtures are described by Priske, M. et al.: Reaction integrated separation of homogeneous catalysts in the hydroformylation of higher olefins by means of organophilic nanofiltration. Journal of Membrane Science, Volume 360, Issues 1-2, 15 Sep. 2010, pages 77-83; doi:10.1016/j.memsci.2010.05.002.

In the membrane filtration of reactor discharges of hydroformylations, the synthesis gas frequently dissolved or not dissolved in the liquid reactor discharge is a peculiarity: The hydroformylation is a two-phase reaction, hydrogen and carbon monoxide form the gas phase, the alkenes, aldehydes and alcohols form the liquid phase in which the catalyst is dissolved solids-free. In accordance with the solution equilibrium in the reactor, also some of the synthesis gas is dissolved in the liquid reactor phase and is taken off together with the reactor discharge. While the synthesis gas remains dissolved in the reactor discharge during the membrane filtration, the membrane filtration is to this extent problem-free. However, if the liquid reactor discharge is accompanied by a gas phase or if, on relaxation of the membrane, a gas phase forms bubbles, the gas bubbles may damage the membrane mechanically. Polymer membranes in particular are susceptible to damage by gas bubbles.

A further problem due to outgassing synthesis gas is the loss of carbon monoxide: In particular in the Rh-catalyzed hydroformylation, the CO partial pressure exerts a critical effect on the activity and stability of the catalyst complex. In order, during the membrane separation of homogeneously dissolved complex catalysts from the reaction discharge of a hydroformylation, to avoid the loss of activity, EP1931472B1 proposes ensuring a minimum CO partial pressure at all three connections of the membrane separation unit (feed, retentate, permeate).

WO2010023018A1 shows two parallel-connected jet loop reactors with a shared external liquid circuit. The jet loop reactors are used in the hydroformylation with homogeneously dissolved catalysts. Separating off the catalyst is not a subject of discussion.

Janssen, M., Wilting, J., Müller, C. and Vogt, D. (2010), Continuous Rhodium-Catalyzed Hydroformylation of 1-Octene with Polyhedral Oligomeric Silsesquioxanes (POSS) Enlarged Triphenylphosphine. Angewandte Chemie International Edition, 49: 7738-7741. doi: 10.1002/anie.201001926 describe carrying out a homogeneously catalyzed hydroformylation in a special spray mist reactor which comprises two external liquid circuits contacting one another in a cross-flow chamber. In a first circulation, the liquid reactor discharge is taken off from the reactor with the synthesis gas dissolved therein and circulated by means of a vane pump. In a cross-flow chamber, the reactor discharge is divided into two substreams: A first substream containing the liquid reactor discharge with dissolved synthesis gas is conducted as synthesis gas in gas phase along the first circulation back into the reactor. A second purely liquid substream is transported by means of a pump through a ceramic membrane separation unit. There, the target product is taken as permeate, the catalyst-containing retentate is passed via the second circulation line back to the cross-flow chamber and there mixed with the first liquid circulation. The advantage of this device is considered that the reactor discharge is degassed within the cross-flow chamber and therefore any gas phases produced remain in the first circulation. This is because the particular flow conditions of the cross-flow chamber favour take-off of the gas bubbles into the reflux of the first circuit. The second liquid circuit in which the membrane is arranged therefore remains gas free (this means $H_2$ and CO remain dissolved in the liquid). However, the disadvantage of this laboratory apparatus is its comparatively complicated structure, the requirement for two pumps and the high fluid-dynamics energy loss in the cross-flow chamber: It is scarcely economic to carry out hydroformylations on an industrial scale using this device.

A device of the generic type mentioned at the outset is known from WO2013/034690A1. Here, the membrane separation unit is arranged in the external liquid circuit of the jet loop reactor. A disadvantage of this device is that the fluid conducted via the external liquid circuit, in addition to the liquid fractions, also transports gas fractions—dissolved in a liquid phase or situated in a gas phase. Therefore, the volume which must be conducted through the membrane separation unit is relatively large. The high feed volume flow rate for the membrane separation unit requires a high membrane surface area and therefore relatively high capital costs for erecting the system. Furthermore, some membrane materials are not at all available in large quantities such that membrane separation units with large membrane surface areas made thereof would be able to be constructed economically.

With respect to this prior art, the object of the invention is to reduce the costs of the device.

This is achieved surprisingly by providing an additional apparatus, namely a gas separator, which is arranged in the external liquid circuit of the jet loop reactor and is installed for separating off gas from the external liquid circuit and feeding it back into the jet loop reactor.

The invention therefore relates to a device for the continuous homogeneous catalytic reaction of a liquid with a gas and optionally a further fluid, wherein the device comprises at least one jet loop reactor having an external liquid circuit driven by at least one pump, wherein the device has at least one membrane separation unit, preferably retaining the homogeneous catalyst, which membrane separation unit is arranged in the external liquid circuit of the jet loop reactor, and wherein a gas separator is arranged in the external liquid circuit of the jet loop reactor, which gas separator is installed for separating off gas from the external liquid circuit and feeding it back into the jet loop reactor.

The invention is based on the knowledge that gas fractions may be removed from the external liquid circuit by means of the gas separator before the liquid circuit is passed to the membrane. A gas separator can separate off, from the fluid conducted in the liquid circuit, not only gas which is dissolved in a liquid phase, but also gas which forms a separate gas phase (bubbles). Degassing in the gas separator decreases the feed volumetric flow rate to the membrane separation unit, as a result of which the membrane surface area and therefore the costs of the membrane separation unit can also be reduced. Since a gas separator is a standard apparatus which is available relatively cheaply and simply, the combination of a membrane separation unit with an upstream gas separator and reduced membrane surface area is less expensive than a conventional device without gas separator but which requires a higher membrane surface area. According to the invention, the membrane surface area of the membrane separation unit is less than in the prior art for the same separation efficiency of the membrane separation unit.

A further advantage of the gas separator is that many commercially available membrane modules are unsuitable for reaction mixtures with dissolved and/or non-dissolved gas fractions, since these are not designed for sufficient gas removal on the permeate side and, depending on the amount of the gas volumetric stream to be removed on the permeate side build up a counterpressure on the permeate side, which decreases the liquid permeate output, or can even lead to destruction of the membrane.

In order to avoid deactivation of the catalyst and damage to the membrane due to degassing, and also to achieve an improved membrane retention, it was customary in conventional systems to degas the permeate of the membrane separation unit. Such measures, thanks to the gas separator according to the invention, are no longer absolutely necessary, since harmful gas fractions are already removed before the membrane separation unit. In contrast to the prior art, the degassing proceeds according to the invention on the feed side and not on the permeate side. A permeate-side post-degassing, however, can be necessary despite preceding degassing, if a homogeneous catalyst must be stabilized during the membrane separation with dissolved gas.

A particular development of the invention provides that in the external liquid circuit, upstream of the membrane separation unit, a heat exchanger is arranged for cooling the feed of the membrane separation unit, and that the gas separator is arranged downstream of the heat exchanger upstream of the membrane separation unit. Such a heat exchanger serves for removing the heat of reaction of exothermic reactions. It makes sense to arrange the gas separator downstream of the heat exchanger, since the liquid circuit then has a lower temperature, and so it may be better degassed. Furthermore, higher temperatures in many membrane materials lead to a reduction of the membrane retention and thereby to an impairment of the separation.

The pump for moving the external liquid circuit is preferably likewise arranged upstream of the membrane separation unit. In particular, it is also arranged upstream of the gas separator and—if a heat exchanger is provided in the liquid circuit—upstream of the heat exchanger.

A preferred development of the invention provides that the membrane separation unit is constructed as a multistage membrane cascade. The permeate quality may be improved thereby and/or the membrane surface area decreased.

As a membrane cascade, in this case, a Christmas tree interconnection or a feed-and-bleed system, such as, in particular, an enrichment cascade or a stripping cascade, comes into consideration.

In the simplest case, the membrane separation unit is constructed as a feed-and-bleed system having a single recirculation circuit (what is termed a loop). In the recirculation circuit, some of the retentate is fed back into the feed.

The permeate quality can firstly be improved in that the membrane separation unit is constructed of a plurality of serial loops.

In addition, the permeate quality can be improved in that a multistage feed-and-bleed system is used as a membrane separation unit. In this case, it is a multistage membrane cascade which has a plurality of recirculation circuits or loops. Cascaded feed-and-bleed membrane systems can be constructed either as "a stripping cascade" or as "an enrichment cascade". Each stage of such a cascade can be constructed of one or more loops.

In contrast to the "Christmas tree interconnection" familiar in membrane technology and therefore known (Melin/Rautenbach), membrane cascades constructed as feed and bleed systems permit operation under feed conditions varying in quality and/or quantity and/or in the case of membrane performance changing with time. At high concentration factors, a stripping cascade leads to a better overall permeate quality than an enrichment cascade for the same installed membrane surface area. In addition, an enrichment cascade has the disadvantage that the surface area required is more than twice as great compared with a single-stage membrane separation unit. In the case of a stripping cascade, in contrast, virtually any desired membrane surface area can be used between a single-stage membrane separation unit and an enrichment cascade. This is important, in particular, when an enrichment cascade is uneconomic owing to the high membrane surface area required and a single-stage membrane separation unit owing to insufficient separation, is unusable.

Under these preconditions, using a two-stage membrane cascade with partial permeate recycling as a membrane separation unit suggest itself. In this case, the permeate is recycled from the recirculation circuit or the circuits having the poorest permeate quality, which is generally the loops having the highest retentate concentration at the end of the concentration section. This interconnection is termed "two-stage stripping cascade" in membrane technology. The recirculation circuits with permeate recycling at the end of the cascade are also termed concentration loops. An interconnection with concentrate loop with permeate recycling permits a purer overall permeate.

Very particular preferably, the membrane surface area used of the concentrate loops is constructed so as to be smaller than the membrane surface area used of the customary loops. In this manner, without impairing the separation result, the membrane surface area requirement is lowered.

Alternatively, the membrane separation unit is constructed as a two-stage enrichment cascade. A two-stage enrichment cascade is a multistage membrane cascade having partial retentate recycling. In this case the total retentate from the second stage is recycled. Not only the first, but also the second stage of the two-stage enrichment cascade can be constructed of one or more membrane loops. Firstly, the concentrate factors required here are low enough that an enrichment cascade is advantageous owing to the separation result in comparison with a stripping cascade. Secondly, the permeate amounts to be generated and therefore the required membrane surface areas are small enough that an enrichment cascade is economic.

A very particularly preferred embodiment of the invention provides that no transport element is provided between the gas separator and jet loop reactor, in such a manner that the jet loop reactor takes in independently from the gas separator gas separated off from the external liquid circuit. This is because the intense inner fluid stream through the jet loop reactor acts like a water jet pump, in such a manner that without additional units, the gas fractions, separated off in the gas separator, of the external liquid circuit may be recirculated to the reactor. No transport element in this context means that no direct transport element such as a pump is provided between gas separator and jet loop reactor. The transport output is ultimately provided by the pump which generates the external liquid circuit and the flow in the reactor and consequently indirectly causes the water pump effect.

In a further preferred embodiment of the invention, a tubular reaction space extends in the jet loop reactor, into which a jet nozzle for injecting the liquid into the reaction space opens out and also a suction tube for intake of gas opens out conjointly, and at which a baffle plate-shielded take-off for the external liquid circuit is provided.

The jet nozzle in the vertically extending reactor can be directed upwardly or downwardly. The joint opening of jet nozzle and suction tube causes an intense mixing of the liquid and gaseous reaction components (water pump effect). The gas can be drawn in by suction from outside via the suction tube, or from a region within the reaction space in which a gas bell extends. The take-off can be arranged at the top or bottom on the reactor. Shielding of the take-off by the baffle plate decreases the introduction of gas bubbles from the internal liquid circuit into the external liquid circuit. For improvement of the flow dynamics, at least one guide tube which extends concentrically through the reaction space can be provided. As a result, the mixing of the liquid and gaseous phase is intensified. A plurality of guide tubes can also be arranged so as to align one after another. Then, the reaction mixture flows through the guide tube in the main flow direction, is deflected at the end of the guide tube and flows back outside the guide tube. The guide tube represents a structural separation of the two flow directions of the inner loop.

The device according to the invention is suitable in an outstanding manner for the homogeneous catalytic reaction of a liquid with a gas and optionally a further fluid in which at least one target product of the reaction with the permeate of the membrane separation unit is discharged from the liquid circuit.

The invention therefore also relates to a method for the homogeneous catalytic reaction of a fluid with a gas, and optionally a further fluid, wherein the reaction is carried out in a device according to the invention, and wherein at least one target product of the reaction with the permeate of the membrane separation unit is discharged from the liquid circuit.

Thanks to the gas separator, it is possible to process a liquid circuit having a gaseous fraction. This is possible up to a gas fraction of about 30% by volume in the feed of the membrane separation unit. A preferred development of the method according to the invention is therefore that the external liquid circuit upstream of the membrane separation unit is a mixture which comprises a liquid phase and a gaseous phase distributed dispersely therein, wherein volume fraction of the gaseous phase is between zero and thirty percent.

The gas separator, however, also permits the processing of relatively high gas amounts. A preferred development of the method according to the invention is therefore that the external liquid circuit, upstream of the gas separator, is a mixture which comprises a liquid phase and a gaseous phase distributed dispersely therein, wherein volume fraction of the gaseous phase is between thirty and 100 percent. The gas separator then serves for separating off the higher gas fraction in such a manner that downstream after the gas separator in the feed of the membrane separation unit a gas content below 30% by volume is present which does not damage the membrane.

These reactions can be two-phase (liquid/gaseous) or three-phase (liquid/liquid/gaseous or liquid/gaseous/gaseous). In the liquid circuit, small amounts of solids can also be present.

Examples of the reactions which may be carried out are oxidations, epoxidations, hydroformylations, hydroaminations, hydroaminomethylations, hydrocyanations, hydrocarboxyalkylation, aminations, ammoxidation, oximations, hydrosilylations, ethoxylations, propoxylations, carbonylations, telomerizations, metatheses, Suzuki couplings or hydrogenations.

Particularly preferably, the device is suitable for hydroformylation, that is to say for reacting compounds having olefinic double bonds with synthesis gas to form aldehydes and/or alcohols.

The use of the described device for carrying out the said method is likewise subject matter of the invention.

The device according to the invention can be used, inter alia, for the reaction of a liquid with a gas, wherein not only the gas, but also the liquid, have at least one reactant.

The reaction products are discharged in the liquid phase together with the permeate.

In the apparatus according to the invention, reactions can be carried out in the pressure range of 0.2 to 40 MPa (absolute) and in the temperature range of 0 to 350° C. The reaction takes place in this case preferably in the presence of a catalyst homogeneously dissolved in the liquid phase.

Preferably, in the device according to the invention, reactions are carried out in which the catalyst is fed with the liquid feed and is dissolved homogeneously in the liquid product/reactant phase, such as, for example, the production of aldehydes and/or alcohols by hydroformylation of compounds having olefinic double bonds in the presence of cobalt carbonyls or rhodium carbonyls with or without addition of phosphorus-containing ligands.

The selection of the suitable membrane material is to be made with respect to the catalyst complex to be separated off: Since the permeability of a membrane to the various components of the feed that is to be separated is ultimately a function of time (the membrane is not absolutely impermeable to a catalyst, its passage rate is rather markedly slower compared with the other reaction participants), the membrane must be selected in such a manner that it preferentially retains the catalyst complex that is to be separated off.

In the method according to the invention, membranes can be used which are suitable owing to the chemical or physical properties thereof to retain organophosphorus metal complex catalyst and/or free organophosphorus ligand preferably in an extent of at least 50%.

Corresponding membranes belong to the class of nanofiltration membranes. The expression nanofiltration is applied to membrane separation methods which have a separation limit or molecular weight cut-off (MWCO) in the range of 150 g/mol to above 1 nm. The size of the separation limit (or molecular weight cut-off—MWCO) indicates the molecular or particle size of a component that has a membrane retention of 90%.

A customary method of determination of the separation limit is given in Y. H. See Toh, X. X. Loh, K. Li, A. Bismarck, A. G. Livingston, in search of a standard method for the characterisation of organic solvent nanofiltration membranes, J. Membr. Sci., 291 (2007) 120-125.

The membrane retention $R_i$ is calculated from the feed-side concentration of the component i in question of the membrane $X_{iF}$ and the permeate-side concentration of the component i in question of the membrane $x_{iP}$ as follows:

$$R_i = 1 - x_{iP}/x_{iR}$$

Preferably, the membranes for the use according to the invention should have an MWCO of less than 1000 g/mol.

A further precondition for the usability of the membrane is that the membrane must be stable to all compounds present in the reaction mixture, in particular must be stable to the solvents. Membranes are also considered to be stabile which—for instance caused by swelling of the membrane polymer—experience a change with time in MWCO and/or permeability, but meet the separation task over the operating period. Furthermore, the membrane material should withstand the reaction temperature. Membrane materials which are stable to the reaction temperature and perform at the reaction temperature permit complex temperature control to be dispensed with.

Preference is given to using membranes having a separation-active layer of a material selected from cellulose acetate, cellulose triacetate, cellulose nitrate, regenerated cellulose, polyimides, polyamides, polyether ether ketones, sulphonated polyether ether ketones, aromatic polyamides, polyamide imides, polybenzimidazoles, polybenzimidazolones, polyacrylonitrile, polyaryl ether sulphones, polyesters, polycarbonates, polytetrafluoroethylene, polyvinylidene fluoride, polypropylene, polydimethylsiloxane, silicones, polyphosphazenes, polyphenyl sulphides, polybenzimidazoles, Nylon® 6,6, polysulphones, polyanilines, polyurethanes, acrylonitrile/glycidyl methacrylate (PANGMA), polytrimethylsilylpropynes, polymethylpentynes, polyvinyltrimethylsilane, alpha-aluminas, titanium oxides, gamma-aluminas, polyphenylene oxide, silicon oxides, zirconium oxides, ceramic membranes hydrophobized with silanes, as described in DE10308111, polymers having intrinsic microporosity (PIM) such as PIM-1 and others, as described, for example, in EP 0 781 166 and in "Membranes" by I. Cabasso, Encyclopedia of Polymer Science and Technology, John Wiley and Sons, New York, 1987. The abovementioned substances may be present, especially in the separation-active layer, optionally in cross-linked form through addition of auxiliaries, or be provided in the form of what are called mixed matrix membranes with fillers, for example carbon nanotubes, metal-organic frameworks or hollow spheres, and particles of inorganic oxides or inorganic fibres, for example ceramic fibres or glass fibres.

Particular preference is given to using membranes having, as a separation-active layer, a polymer layer made of polydimethylsiloxane, polyimide, polyamide imide, acrylonitrile/glycidyl methacrylate (PANGMA), polyamide or polyether ether ketones, which are made up of polymers having intrinsic microporosity (PIM) such as PIM-1, or wherein the separation-active layer is made up by a hydrophobized ceramic membrane. Very particularly preferably, membranes made of silicones or polyamide imide are used. Membranes of this kind are commercially available.

As well as the abovementioned materials, the membranes may include further materials. More particularly, the membranes may include support or carrier materials to which the separation-active layer has been applied. In such composite membranes, a support material is still present as well as the actual membrane. A selection of support materials is described by EP0781166, to which reference is made explicitly.

A selection of commercially available nanofiltration membranes are the MPF and Selro series from Koch Membrane Systems, Inc., different types of Solsep BV, the Starmem™ series from Grace/UOP, the DuraMem™ and PuraMem™ series from Evonik Industries AG, the NanoPro series from Bio-Pure Technology, the HITK-T1 from IKTS, and also oNF-1, oNF-2 and NC-1 from GMT Membrantechnik GmbH.

When jet loop reactor and membrane separation unit are arranged in a shared external liquid circuit, this has the effect that the throughput through reactor and membrane must be identical. For apparatus-specific reasons, however, the throughput performance of reactor and membrane can be different. In order then, nevertheless, to effect a liquid circuit or ideal membrane overflow, it is possible to equip the apparatus having the low throughflow performance with a bypass conduit which permits a partial bypass of the hydraulic obstacle. Accordingly, the device has at least one bypass conduit which is arranged in the external liquid circuit in parallel to the jet loop reactor or to the membrane separation unit.

In a further preferred embodiment of the device, it has not only one jet loop reactor, but rather a plurality of jet loop reactors connectable in parallel having a shared external liquid circuit, wherein the membrane separation unit is arranged within the shared external liquid circuit. A plurality of jet loop reactors which are dimensioned to be specifically smaller permits flexible adaptation of the conversion performance of the device at the demand position by switching individual reactors on and off. This permits economic utilization of the device under changing demand.

The membrane separation unit can accordingly also be constructed to operate in parallel: By switching on and off individual parallel-connected membrane modules, the entire membrane surface area of the membrane separation unit can be flexibly adapted to the system capacity. A preferred development of the invention is therefore characterized by a membrane separation unit which comprises a multiplicity of membranes connectable in parallel in such a manner that the entire active membrane surface area of the membrane separation unit is adjustable by switching the membranes on and off.

The invention will now be illustrated in detail by exemplary embodiments. The figures show.

Figure 1:
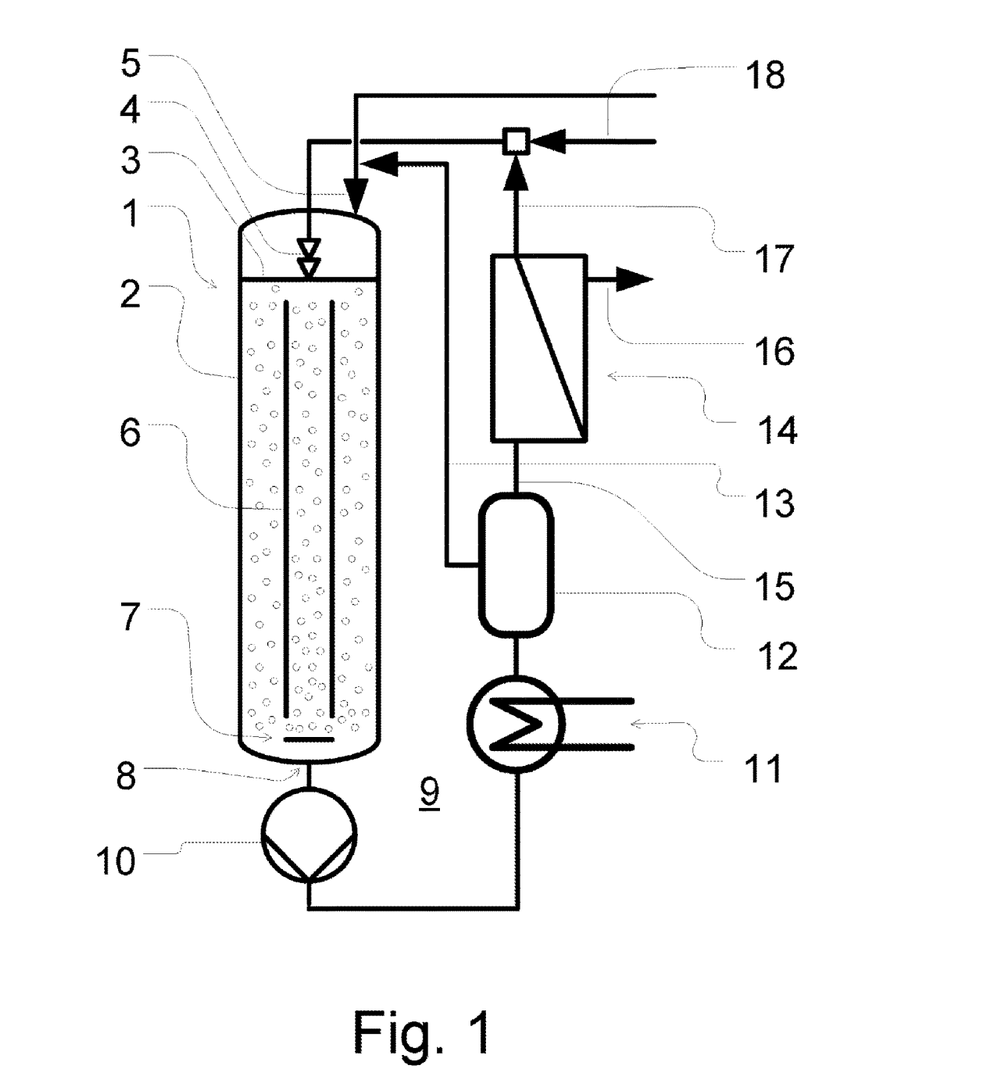
FIG. 1: Device according to the invention having a simple membrane separation unit.

FIG. 1 shows a first embodiment of the device according to the invention having one jet loop reactor 1. The jet loop reactor 1 comprises a tubular reaction space 2 in the form of a pressure tube which is filled with liquid reaction mixture up to a defined liquid surface 3. Above the liquid surface a gas bell of gaseous reaction participants forms. On account of the solution equilibrium, the gaseous reaction participants are in part dissolved in the liquid reaction mixture; in part gaseous reaction participants are situated as gas phase in the liquid (in the drawing shown as gas bubbles). Likewise dissolved in the reaction liquid is the homogenous catalyst.

A jet nozzle 4 downwardly projects into the liquid reaction mixture, via which jet nozzle liquid reaction participants are injected with high kinetic energy. Gaseous reaction participants pass through a gas feed 5 into the reaction space 2. Structurally assigned to the jet nozzle 4 is a suction tube which draws in by suction the gas from the gas-filled part of the reaction space 2 and mixes it with the fluid stream. For this purpose the openings of suction tube and jet nozzle are closely adjacent and jointly open into the reaction space. Owing to the high flow velocity of the liquid reaction participants emerging from the jet nozzle 4, the gaseous reaction participants coming from the gas feed 5 are entrained (comparable to a water jet pump).

A guide tube 6 extends through the reaction space 2 concentrically and coaxially to the pressure tube. The guide tube 6 serves to provide an internal liquid circuit within the reaction space 2: The injected reaction liquid flows from the jet nozzle 4 down through the guide tube 6 and is deflected by the baffle plate 7 that is arranged at the other end of the reaction space 2, in such a manner that the stream flows up again outside the guide tube 6. In this manner, an internal liquid circuit is formed within the reaction space 2, in which liquid circuit the reaction partners are intensively mixed and reacted.

Below the battle plate 7, a take-off 8 is provided, through which reaction mixture is continuously taken off from the reaction space 2 and fed into an external liquid circuit 9. The baffle plate 7 shields the take-off 8 from the internal liquid circuit, in such a manner that gas bubbles scarcely arrive in the external liquid circuit 9. The external liquid circuit therefore predominantly consists of liquid reactants, dissolved catalyst and dissolved gaseous reactants.

For the practical implementation of the invention, it is irrelevant whether jet nozzle 4 is directed downwards and baffle plate 7 is arranged below the jet nozzle 4. It is also possible to inject upwardly from the bottom of the reactor. The take-off can in both cases be arranged at the top or bottom in the reactor. The baffle plate must be arranged accordingly in such a manner that it shields the take-off.

The external liquid circuit 9 is moved by a pump 10. The pump 10 is a peripheral impeller pump which is also able to transport liquid/gaseous mixtures. Minor gas bubbles are therefore harmless.

Downstream after pump 10 a heat exchanger 11 is arranged, by means of which, depending on the type of reaction, heat can be introduced into or discharged from the external liquid circuit 9. Furthermore, the jet loop reactor 1 itself can be provided with a heat exchanger which encloses the reaction space (which is not shown). When exothermic reactions are carried out such as, for example hydroformylations, the heat of reaction is removed by the heat exchanger 11. The heat exchanger 11 then cools the external liquid circuit 9.

Downstream after the heat exchanger 11, a gas separator 12 is arranged. The gas separator 12 separates off gas fractions from the external liquid circuit 9 and feeds these to the jet loop reactor 1. For this purpose, the gas separator 12 is connected via a gas conduit 13 to the gas feed 5 of the jet loop reactor 1. In the gas conduit 13, no transport element is arranged, since the jet loop reactor draws in by suction independently the gas which is separated off from the gas separator 12.

Downstream after the gas separator 12, a membrane separation unit 14 is arranged. As with any membrane, the membrane separation unit 14 has three connections, namely feed 15, permeate 16 and retentate 17. The reaction mixture inflowing via the feed 15 is separated at the membrane into permeate 16 and retentate 17. Since the membrane is less permeable to the dissolved catalyst complex than to the remaining components of the feed 15, the catalyst remains on this side of the membrane and is enriched in the retentate 17. With respect to the catalyst, the membrane separation unit 14 has a better permeability of the products of value, in such a manner that the products of value are enriched with respect to the catalyst in the permeate 16. The permeate 16 is further conducted for treatment (not shown in FIG. 1); the catalyst-rich retentate 17 is returned, mixed with fresh liquid reagent 18, via the jet nozzle 4 into the reactor 1.

The gas separator 12 that is arranged according to the invention upstream of the membrane separation unit 14 effects a decrease of the volumetric flow rate of the feed 15 to the membrane separation unit 14, since gas bubbles and dissolved gas are separated off from the liquid circuit 9 and recirculated via the gas conduit 13 directly into the jet loop reactor 1. Owing to the decreased feed volumetric flow rate, the membrane surface area of the membrane separation unit 14, for the same separation performance, can be smaller than in conventional systems without gas separator 12. In particular, carrying out homogeneously catalyzed hydroformylations becomes markedly more economical since the separation of rhodium phosphite complex catalysts used in this case requires expensive membranes.

In FIG. 1, the membrane separation unit 14 was shown in its most simple design having only one membrane. In practice, the membrane separation unit 14 is rather constructed as a multistage membrane cascade, as shown in FIGS. 2 and 3.

Figure 2:
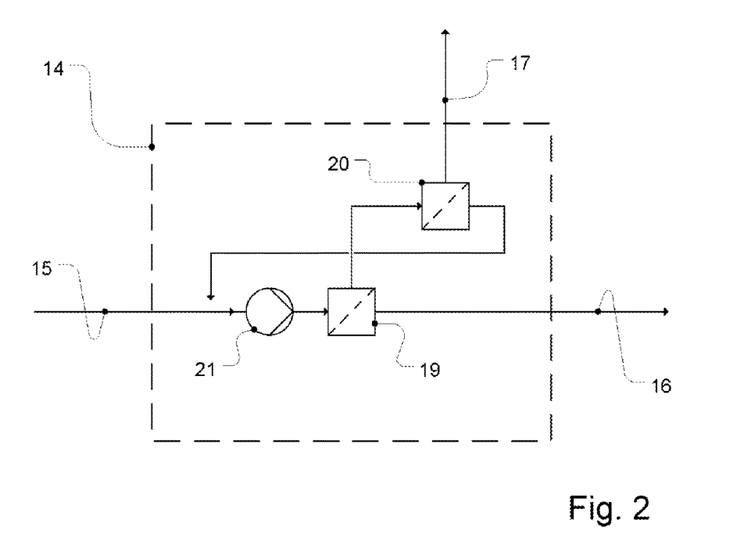
FIG. 2: Detail view of a membrane separation unit as a two-stage stripping cascade.

FIG. 2 shows the fundamental structure of a membrane separation unit 14 designed as a two-stage stripping cascade having two stages 19, 20. The degassed feed 15 is applied to the first stage 19. The permeate of the first stage 19 corresponds to the resultant permeate 16 of the membrane separation unit 14. The retentate of the first stage 19 is applied without further pressure elevation to the second stage 20. The retentate of the second stage 20 corresponds to the resultant retentate 17 of the membrane separation unit 14. The permeate of the second stage 20 is mixed with the feed 15 of the membrane separation unit 14 and fed via an internal pump 21 back to the first stage 19. The permeate of the second stage 20 therefore corresponds to the internal permeate reflux of the membrane separation unit 14 constructed as a stripping cascade.

Figure 3:
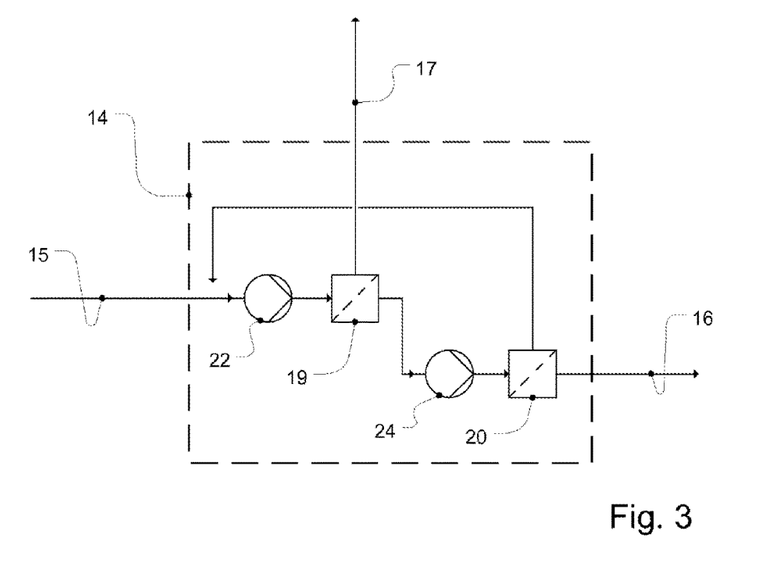
FIG. 3: Detail view of second membrane unit as two-stage enrichment cascade.

FIG. 3 shows the fundamental structure of a membrane separation unit 14 designed as a two-stage enrichment cascade having two stages 19, 20. The degassed feed 15 is applied to the first stage 19. The retentate of the first stage 19 corresponds to the resultant retentate 17 of the membrane separation unit 14 and leaves this. The permeate of the first stage 19 is repressurized by means of a second pressure elevation pump 24 in order to reequilibrate the transmembrane pressure of the first stage 19. Thereafter, the second stage 20 of the membrane separation proceeds. The permeate produced in this case corresponds to the resultant permeate 16 of the overall membrane separation unit 14. The retentate of the second stage 20 is mixed with the feed 15 and recirculated via a first pressure elevation pump 22 to the first stage 19. The retentate of the second stage 20 is therefore the internal retentate reflux of the enrichment cascade.

Figure 4:
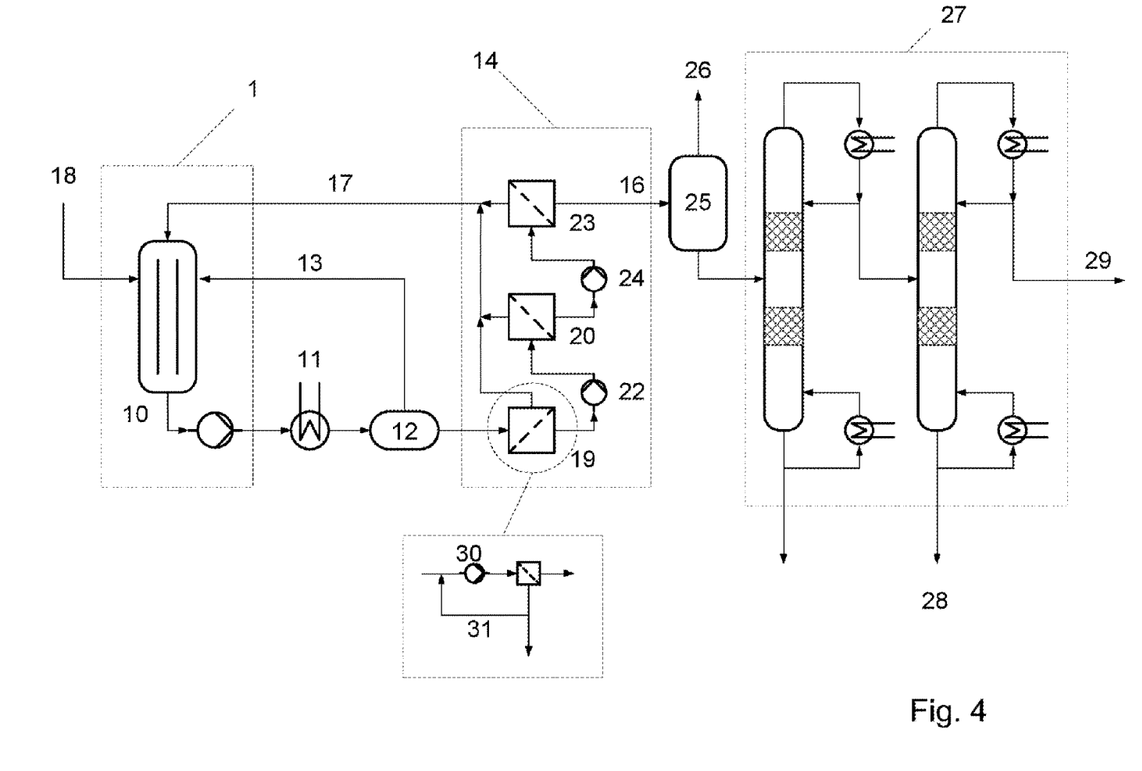
FIG. 4: Device according to the invention having membrane separation unit in cascade and permeate treatment by distillation.

FIG. 4 shows a device according to the invention in which the membrane separation unit 14 has three membrane stages 19, 20, 23 which are connected one after the other in the direction of the permeates thereof. Two pressure elevation pumps 22, 24 equalize the transmembrane pressures that have lowered at the stages 19, 20. The respective retentates of stages 19, 20, 23 are combined as resulting retentate 17 and recycled to the jet loop reactor 1. Each stage 19, 20, 23 also comprises a separate stage pump 30 and an internal loop 31, as shown in the detail enlargement of the first stage 19.

The permeate of the third stage 23 forms the resulting permeate 16 of the membrane separation unit 14. Residual gas components are degassed in a post-degasser 25, which residual gas components had not been separated off by the gas separator 12 for instance for stabilization of the catalyst complex during the catalyst separation via the three stages 19, 20, 23. On account of the pressure drop occurring therebetween, the gas separated off in the post-degasser 25 cannot be recycled to the jet loop reactor 1 without compression, and is therefore, for the sake of simplicity, discarded as off-gas 26.

The gas separated off in the gas separator 12, meanwhile, has still not encountered a membrane, and can therefore be recycled without a transport element via the gas conduit 13 back to the jet loop reactor 1. There, it is fed in separately from the gaseous reactant 18, that is to say not via a shared gas feed.

In FIG. 4, a work-up 27 by distillation of the post-degassed permeate 16 is further shown, in the course of which the actual target products 28, 29 are obtained. The target products are n-butanal 28 and isobutanal 29, which was produced by hydroformylation of propene with carbon monoxide and hydrogen (synthesis gas), all reagent 18. The gas separated off in the gas separator 12 is substantially unreacted synthesis gas.

LIST OF REFERENCE SIGNS 1 jet loop reactor
2 reaction space
3 liquid surface
4 jet nozzle
5 gas feed
6 guide tube
7 baffle plate
8 take-off
9 external liquid circuit
10 pump
11 heat exchanger
12 gas separator
13 gas conduit
14 membrane separation unit
15 feed
16 permeate 17 retentate
18 reagent
19 first stage
20 second stage
21 pump within the membrane separation unit
22 (first) pressure elevation pump
23 third stage
24 second pressure elevation pump
25 post-degasser
26 off-gas
27 work-up by distillation
28 first target product
29 second target product
30 stage pump

What is claimed is:

1. A device for the continuous homogeneous catalytic reaction of a liquid with a gas and optionally a further fluid, wherein the device comprises at least one jet loop reactor having an external liquid circuit driven by at least one pump, and wherein the device has at least one membrane separation unit, retaining the homogeneous catalyst, which membrane separation unit is arranged in the external liquid circuit of the jet loop reactor, wherein a gas separator is arranged in the external liquid circuit of the jet loop reactor, which gas separator is installed for separating off gas from the external liquid circuit and feeding it back into the jet loop reactor.

2. The device according to claim 1, wherein in the external liquid circuit, upstream of the membrane separation unit, a heat exchanger is arranged for cooling the feed of the membrane separation unit, and in that the gas separator is arranged downstream of the heat exchanger upstream of the membrane separation unit.

3. The device according to claim 1, wherein the pump is arranged upstream of the membrane separation unit, the gas separator, and the heat exchanger.

4. The device according to claim 1, wherein the membrane separation unit is constructed as a multistage membrane cascade.

5. The device according to claim 1, wherein no transport element is provided between the gas separator and jet loop reactor, in such a manner that the jet loop reactor takes in independently from the gas separator gas separated off from the external liquid circuit.

6. The device according claim 1, wherein a tubular reaction space extends in the jet loop reactor, into which a jet nozzle for injecting the liquid into the reaction space opens out and also a suction tube for intake of gas opens out conjointly, and at which a baffle plate-shielded take-off for the external liquid circuit is provided.

7. A method for the homogeneous catalytic reaction of a liquid with a gas and optionally a further fluid, wherein the reaction is carried out in a device according to claim 1, and in that at least one target product of the reaction is discharged from the liquid circuit with the permeate of the membrane separation unit.

8. The method according to claim 7, wherein the external liquid circuit, upstream of the membrane separation unit is a mixture which comprises a liquid phase and a gaseous phase distributed dispersely therein, wherein volume fraction of the gaseous phase is between zero and thirty percent.

9. The method according to claim 7, wherein the external liquid circuit, upstream of the gas separator, is a mixture which comprises a liquid phase and a gaseous phase distributed dispersely therein, wherein volume fraction of the gaseous phase is between thirty and 100 percent.

10. The method according to claim 7 wherein oxidations, epoxidations, hydroformylations, hydroaminations, hydroaminomethylations, hydrocyanations, hydrocarboxyalkylation, aminations, ammoxidation, oximations, hydrosilylations, ethoxylations, propoxylations, carbonylations, telomerizations, metatheses, Suzuki couplings or hydrogenations are carried out in the device.

11. The method according to claim 10, wherein compounds having olefinic double bonds are reacted by hydroformylation with synthesis gas to form aldehydes and/or alcohols.

* * * * *